United States Patent [19]

Nevyas

[11] 4,325,375
[45] Apr. 20, 1982

[54] INSTRUMENT FOR INSERTING AND REMOVING INTRAOCULAR LENS

[76] Inventor: Herbert J. Nevyas, 1414 June La., Narberth, Pa. 19072

[21] Appl. No.: 149,070

[22] Filed: May 12, 1980

[51] Int. Cl.³ ............................................. A61B 17/28
[52] U.S. Cl. ................................... 128/321; 294/19 R
[58] Field of Search .................. 128/321, 303 R, 356, 128/305, 322, 325, 354; 81/346, 428 R; 294/104, 19 R, 22, 1 CA; 433/157, 159

[56] References Cited

U.S. PATENT DOCUMENTS

| | | | |
|---|---|---|---|
| 818,869 | 4/1906 | Calvert | 81/346 X |
| 1,085,953 | 2/1914 | Townsend | 128/324 |
| 1,528,717 | 3/1925 | Williams | 128/321 |
| 2,137,635 | 11/1938 | Tyler | 128/321 X |
| 2,137,710 | 11/1938 | Anderson | 128/321 |
| 2,751,908 | 6/1956 | Wallace | 128/321 |
| 3,760,810 | 9/1973 | Van Hoorn | 128/320 |
| 3,882,854 | 5/1975 | Hulka et al. | 128/6 |
| 3,911,923 | 10/1975 | Yoon | 128/303 A |
| 3,921,641 | 11/1975 | Hulka | 128/321 |
| 3,934,589 | 1/1976 | Zimmer | 128/303.1 |
| 3,967,625 | 7/1976 | Yoon | 128/326 |
| 4,170,043 | 10/1979 | Knight et al. | 128/321 X |

OTHER PUBLICATIONS

Karickhoff, John R. "Director for the Choyce Implant" Am. Jour. of Opthalm. vol. 87, No. 4, Apr. 1979, pp. 569-570.

Primary Examiner—Michael H. Thaler
Attorney, Agent, or Firm—Seidel, Gonda, Goldhammer & Panitch

[57] ABSTRACT

The instrument is small and has a pair of jaws manipulable by the use of only two fingers on one hand for inserting and/or removing intraocular lens having centering strands. One jaw is fixed to one end of a tubular member. The other jaw is fixed to one end of a rod or tube extending through the tubular member. The other end of the tubular member is fixed to a base plate. An actuator plate is fixed to the rod or tube and adjacent to the base plate.

7 Claims, 5 Drawing Figures

INSTRUMENT FOR INSERTING AND REMOVING INTRAOCULAR LENS

BACKGROUND

A wide variety of medical instruments having a pair of manipulable jaws are known. For example, see U.S. Pat. Nos. 1,085,953; 3,828,791; and 1,528,717. None of said instruments are entirely satisfactory for use in implanting and removing intraocular lenses having centering strands or support loops of the type disclosed in U.S. Pat. No. 4,159,546.

There is a need for an instrument for inserting and removing intraocular lenses having centering strands which is capable of firmly grasping the lens so that it may be placed behind the iris in one controlled movement in a manner which is safe and reliable.

SUMMARY OF THE INVENTION

The present invention is directed to an instrument for inserting and removing intraocular lens of the type having centering strands. The instrument includes first and second jaws shaped to grasp such an intraocular lens. The instrument includes a tubular member having a first jaw fixed at one end thereof. The second mating jaw is connected to one end of a rod or tube which extends through said tubular member. A base plate is secured to the other end of said tubular member. An actuator is connected to the other end of said rod or tube at a location adjacent the base plate. The base plate and actuator are arranged to facilitate cooperative manipulation by a pair of fingers to oscillate said rod or tube and thereby open or close said jaws.

It is an object of the present invention to provide an instrument for inserting and removing intraocular lenses having centering strands and which allows the lens to be placed behind the iris in one controlled movement which is safe and reliable.

It is another object of the present invention to provide an instrument for making it easier to withdraw an intraocular lens having centering strands particularly if the lens is withdrawn through a somewhat miotic pupil.

It is another object of the present invention to provide an instrument for inserting and removing intraocular lenses which is manipulable by only using the thumb and forefinger on one hand.

It is another object of the present invention to permit the opening and closing of the jaws of the distal end of the instrument without causing a widening or gaping of the wound.

Other objects will appear hereinafter.

For the purpose of illustrating the invention, there is shown in the drawings a form which is presently preferred; it being understood, however, that this invention is not limited to the precise arrangements and instrumentalities shown.

DETAILED DESCRIPTION

Figure 1:
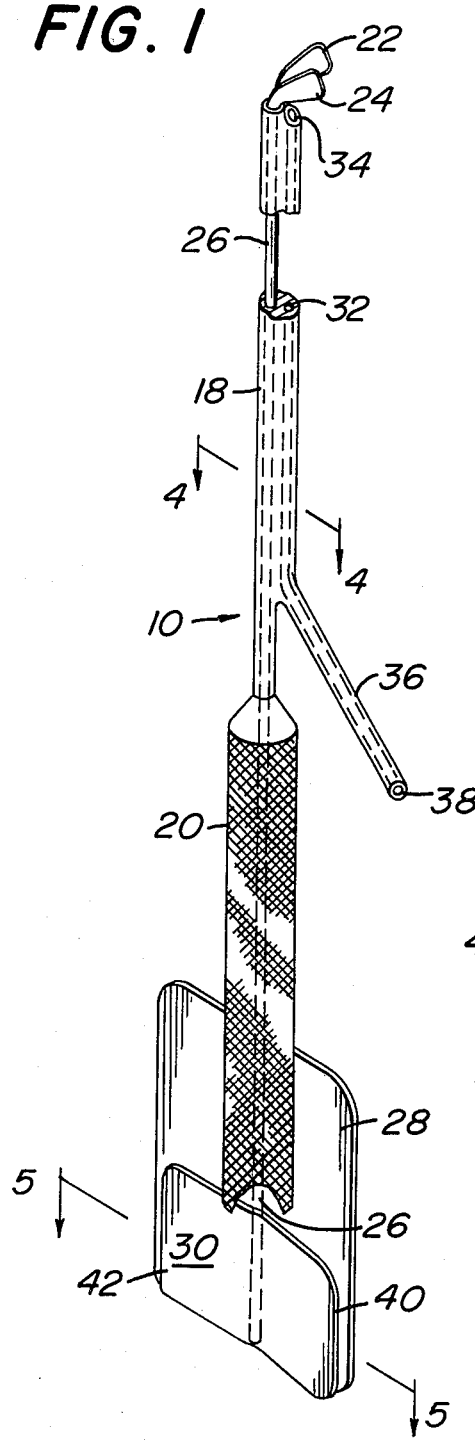
FIG. 1 is a perspective view of the instrument of the present invention with portions broken away for purposes of illustration.

Referring to the drawings in detail, wherein like numerals indicate like elements, there is shown in FIG. 1 an instrument in accordance with the present invention designated generally as 10. The instrument 10 is adapted for inserting and removing intraocular lens 12 having centering strands 14 and 16 of the type disclosed in U.S. Pat. No. 4,159,546 or an equivalent thereof. The centering strands 14, 16 are made from any one of a wide variety of materials which are resilient and have a spring-like memory such as polypropylene. The strands 14, 16 provide support for the lens 12 and act to center the lens behind the iris.

The instrument 10 is preferably short in length. A suitable length for the instrument 10 is between 2½ and 3 inches. The instrument 10 includes a tubular member 18 which may have an enlarged diameter portion 20. Portion 20 may be knurled on its outer periphery. A jaw 22 is fixed to one end of the tubular member 18. A mating jaw 24 is adjacent to jaw 22 for cooperation therewith in grasping an intraocular lens 12 during insertion or removal of the latter.

Figure 5:
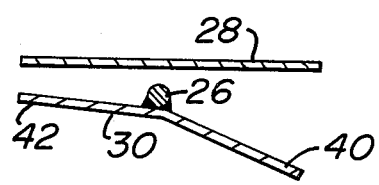
FIG. 5 is a sectional view taken along the line 5—5 in FIG. 1.

The jaw 24 is fixed to one end of a rod or tube 26 which extends through the tubular member 18. Hence, rod or tube 26 is longer than tubular member 18. A generally flat base plate 28 is fixedly secured to the other end of tubular member 18 in any convenient manner such as by welding, brazing, etc. An actuator plate 30 is fixedly secured to the other end of rod 26 in any convenient manner such as by welding, brazing or the like. The actuator plate 30 is adjacent to and smaller than the base plate 28 as will be apparent from FIG. 1. Plate 30 is preferably curved or angled as shown more clearly in FIG. 5 with the rod or tube 26 joined thereto in a central zone thereon.

If desired, the tubular member 28 may have a flow passage 32 brazed or welded thereto. Flow passage 32 terminates in a discharge port 34 adjacent to and between the jaws 22, 24. The other end of flow passage 32 terminates at an inlet portion 38 on an angularly disposed extension 36.

Figure 3:
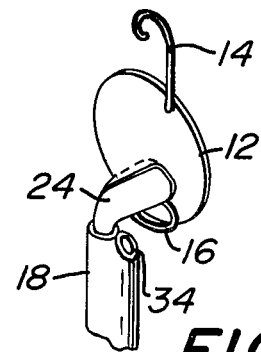
FIG. 3 is a partial perspective view showing how the instrument may be used to grasp both the lens and one of its strands.
Figure 4:
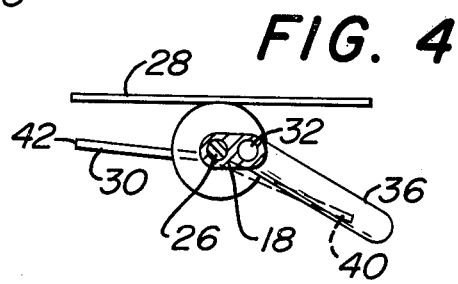
FIG. 4 is a sectional view taken along the line 4—4 in FIG. 1.

By way of example and not by way of limitation, an operative embodiment of the instrument 10 has the following characteristics. The overall length of the instrument 10 is about 2¾ inches long and made from stainless steel. The jaws 22, 24 are thin, flat elements having a length of about ⅛ inch and angularly disposed with respect to the longitudinal axis of rod 26 and tubular member 18 as shown in FIGS. 1 and 3. Rod or tube 26 has an outer diameter of about 0.015 inch while tubular member 18 has an outer diameter of about 0.3 inch. Portion 20 has a length of about 1 inch and a diameter of about ⅜ inch. The base plate 28 has a height of about ⅝ inch and a width of about ½ inch. The actuator plate 30 has the same width as plate 28 but a height which is only one-half the height of plate 28. The plates 28 and 30 are made from stainless steel having a thickness of about 0.03 inch.

Figure 2:
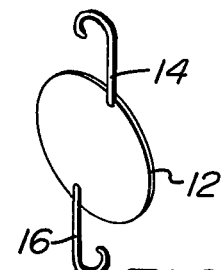
FIG. 2 is a perspective view of an intraocular lens having centering strands.

The instrument 10 is used as follows. With the plates 28 and 30 disposed between the thumb and forefinger, pressure may be applied by the thumb to either side of the plate 30 to thereby oscillate the rod or tube 26 about its longitudinal axis and thereby cause the jaws 22 and 24 to open or close. When the jaws are fully open, edge 42 contacts plate 28. When the jaws are closed, edge 40 contacts plate 28. With the jaws open, one of the centering strands, such as strand 16, is positioned so that it overlies the lens 12 by causing strand 16 to be bent by placing the lens 12 and strand 16 against the distal end of the tubular member 18 adjacent to and between the jaws 24 and 26. Thereafter, the jaws 22 and 24 are utilized to grasp the strand 16 and lens 12 as shown in FIG. 3 for inserting the same into the posterior chamber of an eye following removal of the natural lens such as in cataract surgery. The instrument 10 facilitates grasping the lens and one centering strand firmly as illustrated in FIG. 3 so that such lens may be placed behind the iris in one controlled movement. When the actuator plate 30 is manipulated to open the jaws 22, 24, the folded strand returns to the position as shown in FIG. 2. The instrument 10 is structurally interrelated so that the jaws may open while the jaws are inside the eye and without increasing the size of the incision or damaging the eye. Flow passage 32 may be utilized to irrigate or drain the eye in close proximity to the jaws 22, 24.

The present invention may be embodied in other specific forms without departing from the spirit or essential attributes thereof and, accordingly, reference should be made to the appended claims, rather than to the foregoing specification, as indicating the scope of the invention.

I claim:

1. An instrument for inserting and removing an intraocular lens of the type having centering strands, said instrument comprising first and second jaws being formed and shaped to grasp and manipulate said intraocular lens and hold said centering strands, a tubular member, said first jaw being fixed to one end of said tubular member, a rod extending through said tubular member, said second jaw being fixedly secured to one end of said rod, a base plate secured to the other end of said tubular member, an actuator connected to the other end of said rod at a location juxtaposed to and overlying said base plate, wherein one of said actuator and base plate is generally flat while the other is curved or angled so that the central portion of the actuator is closer to the base plate as compared with the side edges of the actuator, said actuator and base plate being arranged to facilitate cooperative manipulation by only a pair of fingers to oscillate said rod about its longitudinal axis and thereby allow said jaws to be opened, closed and manipulated.

2. An instrument in accordance with claim 1 wherein said jaws extend beyond the end of said tubular member at an acute angle with respect to the longitudinal axis of said tubular member and have a length of about ⅛ inch.

3. An instrument in accordance with claim 1 including means defining a flow passage for the irrigation or drainage of fluids extending longitudinally along said tubular member and terminating at a port adjacent to said jaw.

4. An instrument in accordance with claim 1 wherein said tubular member has an enlarged diameter portion at said other end.

5. An instrument for manipulating an intraocular lens of the type having centering strands comprising an elongated body member, first and second jaws shaped to grasp and manipulate said intraocular lens, said first jaw being fixedly secured to one end of said member, said second jaw being fixedly secured to one end of a rod, said jaws extending beyond the end of said member, said rod being supported by said body member for oscillation about an axis corresponding to the longitudinal axis of said rod, a base plate secured to the other end of said body member and extending therebeyond, an actuator connected to the other end of said rod and extending to opposite sides thereof, said actuator being juxtaposed to the portion of said base plate which projects beyond said body member, said actuator being curved or angled so that the central portion of the actuator is closer to the base plate as compared with side edges of the actuator so that the actuator has pressure zones adjacent its side edges which may be manipulated by only a finger to oscillate said rod and thereby open or close said jaws.

6. An instrument in accordance with claim 5 including a flow passage for the irrigation or drainage of fluids supported by said body member with a port adjacent said jaws.

7. An instrument in accordance with claim 5 wherein said base plate is larger than said actuator.

* * * * *